United States Patent [19]
Roberts et al.

[11] Patent Number: 5,944,684
[45] Date of Patent: Aug. 31, 1999

[54] WEARABLE PERITONEUM-BASED SYSTEM FOR CONTINUOUS RENAL FUNCTION REPLACEMENT AND OTHER BIOMEDICAL APPLICATIONS

[75] Inventors: Martin Roberts, North Hills; David Be-Nyi Lee, Encino, both of Calif.

[73] Assignee: The Regents of the University of California, Oakland, Calif.

[21] Appl. No.: 08/866,972

[22] Filed: Jun. 2, 1997

Related U.S. Application Data

[63] Continuation of application No. 08/521,357, Aug. 31, 1995, abandoned.

[51] Int. Cl.$^6$ ............................................. A61M 37/00
[52] U.S. Cl. ................................. 604/5; 604/4; 604/28; 604/29; 210/646
[58] Field of Search ................................. 604/4, 5, 6, 28, 604/29; 210/259, 638, 646–648, 650–651, 806–807; 128/898

[56] References Cited

U.S. PATENT DOCUMENTS

| | | | |
|---|---|---|---|
| 3,669,880 | 6/1972 | Marantz et al. | 210/259 |
| 3,878,564 | 4/1975 | Yao et al. | 210/321 |
| 4,180,460 | 12/1979 | Calari | 210/182 |
| 4,192,748 | 3/1980 | Hyden | 210/87 |
| 4,317,725 | 3/1982 | Kume et al. | 210/235 |
| 4,338,190 | 7/1982 | Kraus et al. | 210/195.2 |
| 4,474,853 | 10/1984 | Watanabe | 428/403 |
| 4,560,472 | 12/1985 | Granzow et al. | 604/29 |
| 4,618,343 | 10/1986 | Polaschegg | 604/29 |
| 5,039,609 | 8/1991 | Klein | 435/68.1 |
| 5,284,470 | 2/1994 | Beltz . | |

OTHER PUBLICATIONS

Blumenkrantz, Michael J., et al., "An Integrated Approach to the Treatment of Patients with Multiple Organ System Failure Requiring Intensive Nutritional Support and Hemodialysis", (1984) *Trans. Am. Soc. Artif. Intern. Organs*, vol. XXX, pp. 468–472.

Blumenkrantz, Michael J., et al., "Applications of the Redy Sorbant System to Hemodialysis and Peritoneal Dialysis", (1984) *Artificial Organs*, 3(3):.

Bosch, et al., "Filtration Peritoneal Dialysis: A Method to Eliminate Protein Loss", (1983) *Blood Purif.*, 1:154–9.

Caparelli, A.W. et al., "Towards a Wearable Artificial Kidney for Continuous Dialysis: Ex–vivo Sorbant Regeneration of Filtered Peritoneal Dialysate during Intermittent Peritoneal Dialysis," (1993), *Dialysis* 4 (3):399.

Capparelli, A.W. et al., "Protein Loss During Peritoneal Dialysis (PD): Further Studies of Mechanisms and Benefits", (1995), *Periton. Dialysis Int.* 15 (S1):S6.

Curtis,J.R. and Sampson, B. "Aluminum Kinetics during Haemodialysis with the Redy 2000 Sorbsystem", (1989) *Int. J. Artif. Organs*, 12:683–7.

Etteldorf, J.N., et al., "Intermittent Peritoneal Dialysis Using 5 Per Cent Albumin in the Treatment of Salicylate Intoxication of Children", (1961), *J. Ped.* 58 :226–36.

Gordon et al., "Augmentation of Efficiency by Continuous Flow Sorbent Regeneration Peritoneal Dialysis", (1976), *Trans. Am. Soc. Artif. Intern. Organs*, 22:599–603.

Gordon, A. et al. "Sorbent Regenerating of Peritoneal Dialysate: An Approach to Ambulatory Dialysis", (1976–7) *J. Dialysis* 1(2): 145–64.

(List continued on next page.)

*Primary Examiner*—Mickey Yu
*Assistant Examiner*—Francis K. Cuddihy
*Attorney, Agent, or Firm*—Fish & Richardson P.C.

[57] ABSTRACT

A wearable peritoneal dialysis device providing continuous removal of waste metabolites from the blood using a small volume (250–1000 mls) of protein-containing dialysate having an overall flow rate of about 2–3 liters per hour. The device may be worn in several places on the torso and limbs. Included are methods for peritoneal dialysis having improved efficiency, as well as methods for providing hormones, nutrients or therapeutic agents to a patient.

7 Claims, 1 Drawing Sheet

OTHER PUBLICATIONS

Lewin, A., et al., "Sorbent Based Regeneration Delivery System For Use In Peritoneal Dialysis", (1974), *Trans. Am. Soc. Artif. Int. Organs*, 20:130–3.

Lewin, A.J. et al., "Clinical Application of a Sorbent–Based Peritoneal Dialysis Regeneration System", *ASAIO* 5 :48.

Lewin, A.J., et al., "Clinical Application of a Sorbent–Based Peritoneal Dialysate Regeneration System", XIIIth Cong. Abstracts Europ. Dial. Trans. Assoc. 27, Jun. 22, 1976.

Lewin, A.J., et al., "Sorbent Peritoneal Dialysis–Initial Clinical Trials", (1976), *Dial. Transpl. Nephrol.* 13 :284–92.

Lewin, A.J., et al., "Sorbent Based Regenerative Peritoneal Dialysis System", (1978), *Dial. Transplant.* 11 :831–2.

Meehan, et al., "Plasma Sulphate Levels in Haemodialysis Patients with Sorbant Regeneration", (1978) Aust. NZ J. Med., 8:235.

Murisasco et al., "Continuous Arterio–Venous Hemofiltration in a Wearable Device to Treat End–stage Renal Disease", (1986), *Trans. Am. Soc. Artif. Intern. Organs*, 32:567–571.

Neff et al., "A Wearable Artificial Glomerulus", (1979) *Trans. Am. Soc. Artif. Intern Organs*, 25:71–73.

Park, M.S. et al. "Albumin–based Solutions for Peritoneal Dialysis: Investigations with a Rat Model", (1995), *Artificial Organs* 19 (4):307–14.

Pierides and Frohnert, "Aluminum Related Dialysis Osteomalacia and Dementia after Prolonged Use of the Redy Cartridge", (1981), *Trans. Am. Soc. Artif. Intern. Organs*, 27:629–632.

Raja, R.M., et al., "Recirculation Peritoneal Dialysis (RPD) with Sorbent Redy Cartridge", (1974), *Nephr. Cong.* 16 :113.

Roberts, M., et al. "Clinical Results in Patients on the Sorbent Recirculating Dialysate System (Redy) for Over 1 Year", (1974), *Nephr. Congr.* 16 :114.

Roberts, M., et al., "Regeneration of Peritoneal Dialysate (PD): A Step Towards a Continuous Wearable Artificial Kidney (CWAK)", (1991) *J. Am. Nephrol. Soc.* 2 :867.

Roberts, M., "Wearable Artificial Kidneys for Continuous Dialysis", (1993), *ASAIO J.* 39 :19–23.

Roberts, M., et al., "Sorbent Continuous Cyclic (CCPD) and Ambulatory (CAPD) Peritoneal Dialysis: Ex–vivo Clinical Evaluation", (1993) *XIIth Int. Cong. Nephrol.*, p. 312.

Roberts, M., et al., "Development of a Wearable Artificial Kidney Based upon Sorbent Regeneration of Peritoneal Dialysate (PD)", *Periton. Dial. Int.* 15(4):S88.

Roberts, M. et al., "Peritoneal Dialysate (PD) Regeneration Using Commercially Available Redy Sorbent Cartridges: A Practical Means of Optimizing Continuous Cyclic Peritoneal Dialysis (CCPD)",(1994). *J. Am Soc. Nephr.* 5 :426.

Roberts, M., et al., "Ultrafilter Selection for Sorbent Continuous Cyclic (CCPD) and Ambulatory (CAPD) Peritoneal Dialysis", (1993) *ASAIO Abstr.*, p. 115.

Roberts, M. et al. "Continuous Ambulatory Regenerative Dialysis (CARD)" (1992), J. Amer. Soc. Nephrol. 3:102.

Sarnatskaya, V.V., et al., "Peritoneal Dialysis for the Removal of Protein–Bound Markers of Hepatic Insufficiency", (1993) *Artificial Organs* 17 (10):828–36.

Shoji, S., et al., (1988), "Prototype Miniature Blood Gas Analyzer Fabricated on a Silicon Wafer", *Sensors Actuators*, 15:101–7.

Stange et al., Dialysis Against a Recycled Albumin Solution Enables the Removal of Albumin–Bound Toxins, (1993), *Artificial Organs*, 17(9):809–13.

Tada, Y., et al., "A New Approach for the Filtrate Regeneration System in the Wearable Artificial Kidney", (1990) *Artificial Organs*, 14:405–9.

Zalups, R.K., et al., "Factors Affecting Inorganic Mercury Transport and Toxicity in the Isolated Perfused Proximal Tubule", (1991) *J. Am. Soc. Nephrol.* 2 :866–78.

WEARABLE PERITONEUM-BASED SYSTEM FOR CONTINUOUS RENAL FUNCTION REPLACEMENT AND OTHER BIOMEDICAL APPLICATIONS

This is a continuation of application Ser. No. 08/521,357, filed Aug. 31, 1995, now abandoned.

BACKGROUND OF THE INVENTION

Patients with end-stage renal disease (ESRD) are currently treated by kidney transplantation or by dialysis to detoxify the blood. Kidney transplantation involves the surgical replacement of the patient's kidney with a kidney from either a live donor or a cadaver. In order to avoid rejection of the transplanted organ, the recipient patient must receive life-long drug treatment to suppress immune rejection. Even then, the kidney may be rejected and will have to be removed. The patient then will require another transplantation or dialysis.

Treatment by dialysis is performed by either hemodialysis or peritoneal dialysis. In hemodialysis the patient's blood is channeled to a dialyzer which contains a synthetic semi-permeable membrane. Simultaneously, fresh dialysate from an external source is also channeled into the dialyzer where the blood and dialysate are separated by the semi-permeable membrane. The purified blood is then returned to the patient while the used dialysate is discarded. The process takes 3–4 hours and must be repeated three times a week. Hemodialysis performed in this manner is problematic in that normalization of the patient's fluid and electrolyte balance occurs rapidly during the intradialytic period, and then deteriorates during the interdialytic period. Also, the frequency and duration of dialytic treatment potentially curtail normal activities for the dialysis patient.

Attempts have been made to address these problems by performing dialysis continuously with a wearable device. U.S. Pat. No. 5,284,470, issued Feb. 8, 1994 to Beltz, describes a wearable, portable hemodialyzer. Murisasco et al. (1986) Trans. Am. Soc. Artif. Intern. Organs 32:567–571, disclose a wearable continuous hemofiltration device. Neff et al. (1979) Trans. Am. Soc. Artif. Intern. Organs 25:71–73 described a hemofiltration system attached to a patient's forearm. However, presently available hemodialysis systems require the administration of anticoagulants to the patient to prevent clotting of the artificial kidney and the extracorporeal circulation. Nevertheless, even though the anticoagulants are given continuously, clotting occurs within a few days making the continuous systems unusable. In addition, the complications and side-effects of chronic administration of heparin include bleeding, pruritus, allergy, osteoporosis, hyperlipidemia, and thrombocytopenia. Another problem is the finite life-span of the vascular access requiring repositioning of the access and sometimes resulting in loss of all suitable sites making it impossible to continue maintenance dialysis.

Peritoneal dialysis is another form of dialysis which can be used for ESRD patients. Peritoneal dialysis is performed by infusing a sterile, non-pyrogenic dialysis solution into the peritoneal cavity. Waste metabolites in the blood diffuse across the peritoneal membrane into the dialysate. The dialysate containing the waste products is removed immediately or after several hours, discarded and replaced with fresh dialysis solution.

Peritoneal dialysis offers several advantages over hemodialysis in that the patient's blood is not externalized, thereby eliminating the need for anticoagulants and access to blood vessels. However, the efficiency of peritoneal dialysis is low relative to hemodialysis. Also, currently available peritoneal dialysate contains lactate and has a low pH (5.0–5.5). A dialysate containing bicarbonate at a physiological pH (e.g., 7.4) would be preferable. But a stable solution of such composition cannot be produced because it would caramelize when heat sterilized.

The efficiency of peritoneal dialysis can be increased substantially by increasing the dialysate flow rate. This would require large volumes of expensive dialysis solution. Another disadvantage of current peritoneal dialysis practice is the loss of protein with the spent dialysate.

Kraus et al., U.S. Pat. No. 4,338,190, issued Jul. 6, 1982, attempted to eliminate both these disadvantages. To reduce the cost of the dialysate, they prepared the dialysate from concentrate and tap water purified by hyperfiltration. Such a system would require high pressures which may not be safe as a wearable artificial kidney. In addition, the system must be attached to a source of tap water. To eliminate protein loss, they separated the protein from the spent dialysate by means of a membrane having a low permeability to high molecular weight protein and a high permeability to low molecular weight toxic metabolites and return the protein to the patient. However, in this process of dialysate reclamation, no method or provision is made for removal of protein-bound toxins and undesirable proteins, if present.

Currently, there is no dialytic treatment which caters to the removal of protein-bound toxins in renal failure patients. In in vitro tests, Stange et al. (1993) Artif. Organs 17:809–812 demonstrated that by treating a hemodialysis membrane with albumin and adding albumin to the dialysate, protein-bound toxins in human plasma could be dialyzed. In salicylate over-dosed patients (without renal failure) treated with acute peritoneal dialysis, Etteldorf et al. (1961) J. Pediatr. 58:226 reported increased salicylate clearance when albumin is added to the peritoneal dialysate. There has been no attempt to incorporate the removal of protein-bound uremic toxins as a part of the strategy in the dialytic treatment of patients with renal failure, either on an acute or chronic basis. Commercially-available albumin is expensive, may cause allergic and other sensitivity complications, can carry infectious agents and would not be expected to remove uremic toxins bound to proteins other than albumin.

Lewin et al. (1974) Trans. Amer. Soc. Artif. Int. Organs 20:130–133 and Gordon et al. (1976) Trans. Am. Soc. Artif. Int. Organs 22:599–603) attempted to reduce the cost of the large volume of dialysate and also to reduce the volume of solution carried by the patient by regenerating the spent dialysate using a sorbent system. However, they subsequently found that the protein in the spent peritoneal dialysate interfered with the operation of the sorbent system. For a review article, see Roberts (1993) ASAIO J. 39:19–23.

The feasibility of constructing a wearable system has been demonstrated in that small disposable devices have been developed for handling biological samples and conducting certain clinical procedures. Shoji et al. (1988) Sensors Actuators 15:101–107) reported the use of a miniature blood gas analyzer fabricated on a silicon wafer. CIBA Corning Diagnostics Corp. (USA) has manufactured a microprocessor-controlled laser photometer for detecting blood clotting. Micromachining technology has enabled the manufacture of microengineered devices having structural elements with minimal dimensions ranging from tens of microns (the dimensions of biological cells) to nanometers (the dimensions of some biological macromolecule).

SUMMARY OF THE INVENTION

The present invention features a peritoneal dialysis device, with improved efficiency for removal of metabolic wastes from blood, which is wearable and recirculates a small volume of dialysate.

Accordingly, in one aspect, the invention provides a wearable peritoneum-based system for continuous blood cleansing and enrichment, including an inlet for introducing dialysate into the peritoneal cavity of a patient, an outlet for removing dialysate from the peritoneal cavity, a sieve through which the dialysate removed from the peritoneal cavity is passed for removing cellular debris and mucoid material, a hemofilter having a suitable pore size to separate the dialysate into ultrafiltrate and protein-containing fractions, an ultrafiltrate purifier for removing metabolic wastes from the ultrafiltrate fraction, a protein purifier for removing protein-bound toxins and noxious proteins from the protein-containing fraction, a regenerator for recombining the purified ultrafiltrate and protein-containing fractions to regenerate dialysate for introduction into the peritoneal cavity, a sterilizer for sterilizing the regenerated dialysate, and a pump apparatus to circulate the dialysate, the ultrafiltrate and protein-containing fractions through the purifier, and the regenerated dialysate into the peritoneal cavity.

In one embodiment of the invention, the dialysis device contains a reservoir bag for storage of excess fluid removed from the body of the patient.

In one embodiment, the sieve has a pore size of about 1/20th of an inch and the hemofilter is an array of hollow fibers with a pore size such that molecules below 1,500 Daltons are freely passed, while molecules larger than 30,000 Daltons are retained. In a preferred embodiment, the hemofilter has a KuF of 20–100 ml/mm Hg/hr to achieve an optimum filtration rate. Suitable membranes include polyacrylonitrile membranes such as PAN-50-p (Asahi), polysulfone membranes such as Diafilter-20 (Amicon), and HF-500 (Renal Systems), and polyamide membranes such as HF-66 (Gambro). It will be understood that other membranes or devices may be suitable for removal of substances from the dialysate.

By "ultrafiltrate purifier" is meant a combination of sorbent materials for removing urea, ions, and other undesirable unfilterable substances. Preferably, such a purifier will comprise a cartridge having a urease layer to remove urea, a zirconium phosphate layer to remove ammonia, calcium, magnesium, potassium and other cations, a hydrated zirconium oxide layer to remove phosphate and other anions, and an activated carbon layer to remove creatinine, uric acid, and other organic substances. The ultrafiltrate purifier is preferably a packet which is replaced easily and aseptically every 4–8 h. It will be understood that other sorbents and non-sorbent devices may be suitable for removal of toxins and other substances from the ultrafiltrate.

By "protein purifier" is meant a matrix of one or more materials which selectively remove toxic or undesirable substances, e.g., ions and organic compounds bound to the protein and toxic proteins in the protein-containing fraction. Examples of such materials include ion exchangers, Protein A, glomerular basement membrane binding phases, and heparin agarose phases. The protein purifier is preferably a packet that is replaced easily and aseptically every 4–8 h. It will be understood that other matrices and systems may be suitable for removal of protein-bound toxins and undesirable proteins from the protein-containing fraction.

In another embodiment, the device comprises appropriate inlets, reservoirs and pumps for incorporating additional compounds into the regenerated dialysate. Compounds which may be incorporated into the regenerated dialysate include hormones, vitamins, sugars (such as glucose), minerals, and therapeutic agents. It will be understood that the device will comprise appropriate pumps to circulate the dialysate to and from the peritoneum and through the filter, sorbents and connecting lines. This circulation may be provided by a single or plurality of pumps.

The device provides a regenerated dialysate with improved physiological properties, including an improved physiological pH. In addition, the device provides purified proteins which reduce protein-loss from the patient's blood into the peritoneal cavity, reduces the requirement for glucose and other osmotic agents due to the oncotic pressure of the purified protein and increases the clearance of protein-bound toxins by infusing proteins "stripped" of toxins back into the peritoneal cavity. The invention uses a small total dialysate, preferably 250 to 1000 ml.

In another aspect, the invention provides a method for continuous removal of metabolic wastes from the blood of a patient. In the method of the invention, dialysate is introduced into the peritoneal cavity of a patient, where metabolic wastes enter the dialysate from the blood by diffusion, convection and other physiological processes. The used dialysate is removed from the peritoneal cavity, purified, and regenerated. The regenerated dialysate is then reinfused into the peritoneal cavity of the patient.

In one embodiment of the method of the invention, the used dialysate is passed through a sieve for removal of cellular debris and mucoid material prior to passage through the hemofilter.

The used dialysate is purified by passing it through a hemofilter, separating the used dialysate into protein-containing and ultrafiltrate fractions. The protein-containing fraction is purified by removal of protein-bound toxins, generating purified protein. The ultrafiltrate fraction is purified by passage through sorbent materials which remove metabolic wastes, generating purified ultrafiltrate.

In a related aspect, the invention provides a method for continuously infusing a therapeutic agent into the blood of a patient. The removed dialysate is purified to the extent desired, and the therapeutic agent added to the regenerated dialysate. The enriched dialysate is then reinfused into the peritoneal cavity of the patient. By "therapeutic agent" is meant a hormone, nutrient, vitamin, and/or antibiotic or other medication for treatment of a medical condition. This aspect of the invention is applicable for treatment of a wide variety of medical conditions, including, but not limited to, chronic outpatient management of endocrine disorders such as diabetes mellitus, adrenal or pituitary failure, treatment of chronic sepsis with antibiotics, management of intestinal failure with total parenteral nutrition, and the management of bleeding disorders, e.g., continuous, on demand, or scheduled infusion of factor VIII and continuous chemotherapy for conditions such as cancer and AIDS.

Other features and advantages of the invention will be apparent from the following detailed description, and from the claims.

DETAILED DESCRIPTION

Figure 1:
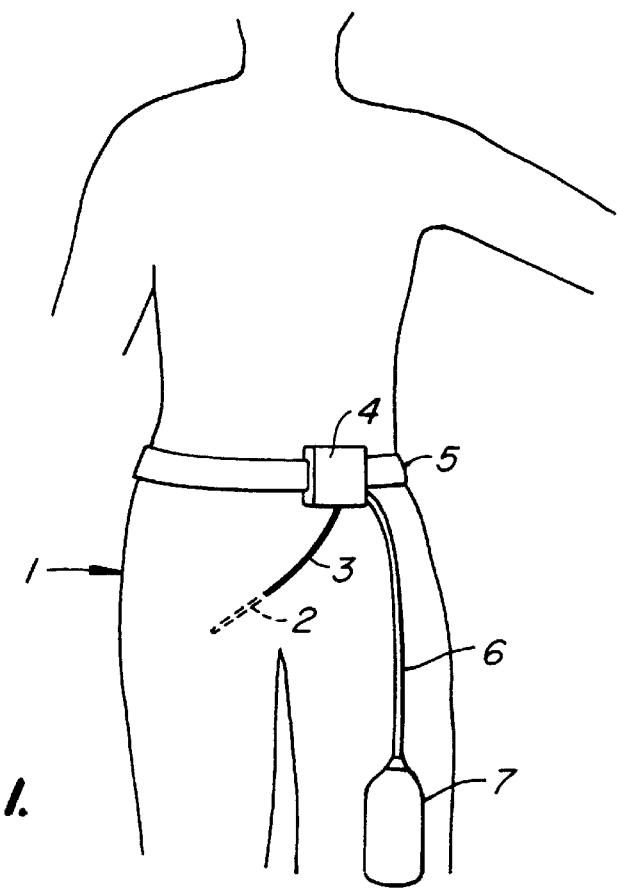
FIG. 1 is a view of a patient wearing the dialysis device as a waistpack.

The present invention provides several important advantages over the prior art, including an improved efficiency of peritoneal dialysis, continuous rather than intermittent removal of waste metabolites from the blood, a reduced dialysate volume, reduced loss of essential blood proteins, and an improved protein-containing regenerated dialysate. Additionally, the peritoneal dialysis device may be worn on different parts of the body, reducing skin irritation and accommodating a wide range of normal activities.

In terms of the clearance of small molecule waste substances, known methods for peritoneal dialysis are generally less efficient than hemodialysis. However, the efficiency of peritoneal dialysis is a function of the overall flow rate of the dialysate. Thus, if sufficient flow of peritoneal dialysate is used, the efficiency of peritoneal dialysis can match or exceed that achieved by hemodialysis. The present invention utilizes an overall flow rate which can be sufficiently high to achieve improved efficiency of removal of waste products.

Many current versions of dialysis devices clear metabolic wastes on an intermittent, rather than continuous basis. The result is a metabolic "see-saw", instead of the natural pattern of steady and continuous clearance. This fluctuation is particularly marked in hemodialysis, but is also inherent in known methods for peritoneal dialysis. For example, continuous ambulatory peritoneal dialysis (CAPD), continuous cycler-assisted peritoneal dialysis (CCPD) and nocturnal intermittent peritoneal dialysis (NIPD) all involve intermittent drainage of spent dialysate and introduction of fresh dialysate in quantities of two or more liters. Blood clearance is therefore achieved in spurts. By contrast, the current invention provides continuous, steady-state removal of metabolic wastes from the blood, thereby approximating the natural kidney function.

Up to now, improved peritoneal dialysis has been difficult to achieve due to a number of factors. The lower efficiency of peritoneal dialysis required use of large volumes of expensive dialysate, as well as resulting in an increased physical demand on a patient due to more frequent dialysate exchange. More frequent exchanges may also be associated with an increased number of infectious episodes. Further, retaining larger quantities of fluid in the peritoneum can increase the incidence of back-pain and abdominal hernias. The present device and method achieve an improved efficiency of peritoneal dialysis by continuously recirculating a relatively small volume of dialysate.

Serum proteins enter the peritoneal cavity by convection through "pores" which do not impose size-hinderance. Thus, the protein-containing fraction separated from used dialysate includes not only beneficial proteins (e.g., albumin) but may also include "noxious" or undesirable proteins (e.g. paraproteins) present in the blood. The present method allows for selectively removing both protein-bound toxins as well as undesirable proteins. However, in contrast to other peritoneal dialysis devices, the present device and method allows for return of beneficial proteins to the patient.

A preferred regenerated dialysate produced and used in the present method, is more advantageous than the commercially available dialysate because it has a pH closer to physiological (pH 6.5–7.5) and contains bicarbonate in place of acetate or lactate. Thus, the regenerated dialysate will be better tolerated by the patient.

The following is a description of a preferred embodiment. Spent dialysate in the outflow is first passed through a sieve, in which large cellular debris and mucoid material, if present, are removed. In one embodiment, the sieve is 1/20th inch nylon mesh. The dialysate is then passed through a hemofilter, preferably of the hollow fiber filter type. The hemofilter allows small molecules to pass through while retaining proteins and other larger molecules. As a result of passage through the hemofilter, the ultrafiltrate is separated in this preparatory phase from the protein and other unfilterable material.

Membranes suitable for use in the hemofilter include any membrane with a pore-size which retains protein. Suitable membranes include polyacrylonitrile membranes such as PAN-50-p (Asahi), polysulfone membranes such as Diafilter-20 (Amicon) and HF-500 (Renal Systems), and polyamide membranes such as FH-66 (Gambro).

The ultrafiltrate is then passed through a purification system which removes metabolic wastes. In one embodiment, the purification system consists of a sorbent cartridge which contains a urease layer for conversion of urea to ammonium carbonate; a zirconium phosphate layer to adsorb ammonia, calcium, magnesium, potassium, and other cations; a hydrated zirconium oxide layer to adsorb phosphate and other anions; and an activated carbon layer to adsorb creatinine, uric acid, and other organic substances. An example of a commercially available ultrafiltrate purifier is the REDY sorbent cartridge (Cobe Renal Care, Inc., Lakewood, Colo.).

The proteins separated from the dialysate in the preparatory phase are detoxified and returned to the patient. It is believed to be a novel feature of the invention that proteins from the patient's spent peritoneal dialysate are separated from the dialysate, purified, and reinfused to enhance transfer of protein-bound toxins from the blood to the peritoneal cavity. The proteins are recycled to remove more toxins. In addition, the proteins, by reverse convection, reduce protein loss in the peritoneal cavity, and provide oncotic pressure resulting in the need for less glucose and other osmotic agents. Undesirable proteins may be selectively removed, for example, by cryofiltration (to remove cryoproteins) or thermofiltration and heparin extracorporeal low-density lipoprotein (LDL) precipitation to remove LDL. Immunoglobulins can be separated from albumin using appropriate filters, or can be selectively adsorbed using protein A columns. The protein purification system allows specific antibodies (for example, "self" antibodies resulting in autoimmune disease) or viral proteins to be selectively removed. In one embodiment, the proteins are passed through a sorbent system which can remove unwanted protein fractions and protein-bound toxins. These sorbents may include zirconium phosphate, hydrated zirconium oxide, activated carbon, ion exchangers, activated aluminum oxide, and protein A.

The purified ultrafiltrate and protein-containing fractions are each reconstituted, as desired. In the preferred embodiment, physiological concentrations of calcium, magnesium, potassium, and glucose are added to the purified ultrafiltrate, however, other desired compounds may be added to the ultrafiltrate or protein-containing fraction. The reconstituted ultrafiltrate and protein-containing fractions are then reunited, thereby completing the regeneration of fresh dialysate (the regeneration phase). The regenerated dialysate is reinfused into the peritoneal cavity, completing one cycle of a continuous process.

The flow rate through the system is typically 2 to 3 1/h, and the total volume of the system is typically between 250–1000 ml.

The present invention may also be used to provide hormones, nutrients, therapeutic and other beneficial agents to the patient. These agents are introduced into the dialysate purified from the sorbent/regeneration columns, from an optional infusion unit, or through other means and devices incorporated into the dialysate circuit. Once in the peritoneum, these beneficial agents can "reverse dialyze" into the bloodstream of the patient through the peritoneal membrane. In one embodiment of this optional repletion phase, nutritional supplementation can be accomplished continuously or intermittently, as desired, to dialysis patients with "failure-to-thrive" syndrome. In otherwise "asymptomatic" hypoalbuminemic dialysis patients, different nutritional strategies may be utilized during this repletion phase to correct the condition. In addition to nutrients, essential renal hormones such as erythropoietin and 1,25-dihydroxyvitamin D can also be provided to the patient at the repletion phase.

Nutrients may also be provided to non-renal patients. For example, the device may be used to provide total parenteral nutrition to patients in need of complete bowel rest over extended periods of time, or to patients who do not have a functional bowel and require life-long parenteral nutrition.

In one embodiment, hormones and therapeutic agents, such as insulin, growth hormone, or antibiotics, are provided on a continuous basis to non-renal patients in need of such agents.

Excess fluid removed for attaining daily fluid balance may be stored in a reservoir bag which can be periodically emptied in a manner similar to periodic urination in normal subjects. Under conditions in which fluid preservation is of critical importance, ultrafiltration can be completely eliminated and "urine" output reduced to zero. The used sorbent cartridge and optional infusion unit can be "unplugged", and fresh units "replugged" in order to maintain the sterility of the wearable system.

The device of the invention is automated, water-proof, and miniaturized into a wearable form contoured to fit unobtrusively into several alternative sites on the surface of the torso and limbs. The choice of alternate body sites allows the patient greater freedom in apparel selection, for purpose of fashion, life-style, and activity preferences.

Referring to FIG. 1, the patient 1 receiving peritoneal dialysis has the artificial kidney 4 connected to an in-dwelling peritoneal catheter 2 which provides access to the peritoneal cavity. A connecting tube 3 provides a pathway from the artificial kidney to the peritoneal catheter. A belt 5 holds the artificial kidney in place on the patient. Alternatively, the artificial kidney may be worn as a backpack, or various components of the artificial kidney may be distributed to various pockets of a garment such as a vest. Excess fluid is conducted via a tube 6 to a leg bag 7 which the patient can periodically empty. In an alternate embodiment, excess fluid is stored in the patient's bladder, which is emptied periodically by urination.

Figure 2:
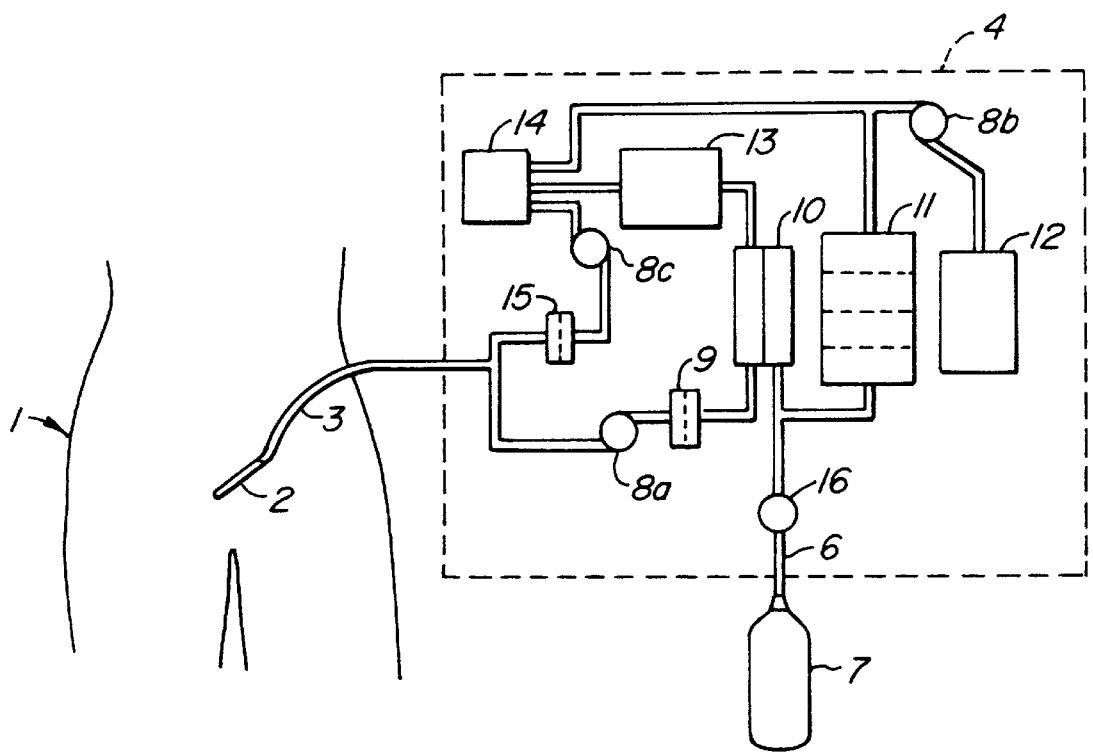
FIG. 2. is a schematic diagram illustrating the components of the dialysis device.

FIG. 2 shows an embodiment of the artificial kidney 4. Initially, 250–1000 ml of dialysate is introduced prior to attaching the device to the patient. Spent dialysate is removed from the peritoneal cavity through catheter 2 and connecting tube 3 by pump 8a through sieve 9, filter 10, protein purifier 13, and storage reservoir 14. Depending on need, part of the ultrafiltrate from 10 is passed by valve 16 into leg bag 7 via tube 6. The remaining filtrate is passed through the ultrafiltrate purifier 11 into reservoir 14. Therapeutic agents stored as concentrates in reservoir 12 which is replugged without breaking sterility are added to the reservoir 14 by means of pump 8b. After 250–500 ml of peritoneal fluid are pumped out of the peritoneal cavity, pump 8a is turned off and pump 8c is activated. The fluid in reservoir 14 is pumped through sterilizing filter 15 into the patient's peritoneal cavity. The entire process is repeated after 250–1000 ml of dialysate have been pumped into the peritoneal cavity. The control of valves and activation/deactivation of pumps are automated by microprocessors (not shown) and powered by a portable power source (not shown). The entire device 4 is enclosed in a waterproof enclosure.

In an alternate embodiment, a double lumen in-dwelling peritoneal catheter is used in place of catheter 2 to provide continuous inflow and outflow. In this embodiment, both pumps 8a and 8c operate simultaneously to provide continuous flow through the peritoneal cavity.

The following examples are presented to set forth more clearly the invention without imposing any limits on the scope of the invention as set forth in the claims.

EXAMPLE 1

Continuous Peritoneal Dialysis in a Patient with Renal Insufficiency.

The spent peritoneal dialysate in the patient's peritoneal cavity is pumped out at a flow rate of 4.5 L/hr through a sieve where particulate matter is withheld, and the fluid passed into a filter which separates the nonfilterable protein fraction from the ultrafiltrate. The outflow of the protein fraction from the filter is controlled at 19–45 ml/h, and passes through the protein purification system to a storage reservoir. The purification system consists of an anion exchanger and activated carbon. The remainder of the fluid passes through the hollow fibers of the hemofilter, and through the ultrafiltrate purification system to the storage reservoir. The purification system consists of a layer of urease followed by layers of zirconium phosphate, hydrated zirconium oxide, and activated carbon. A separate system adds calcium and magnesium acetate to the storage reservoir. After about 500 ml of spent dialysate has been pumped out of the patient's peritoneal cavity, the outlet pump is turned off and an inlet pump takes the fluid out of the storage reservoir, pumps it through a 0.22 micron filter, and into the patient's peritoneal cavity at 9 L/h to give an overall flow rate of 3 L/h. The entire process is repeated after the patient receives 500 ml of fluid.

Example 2

Administration of Insulin to Diabetic Patient.

The peritoneal dialysis is performed as described in Example 1, with the addition of insulin either in a separate container or in the container containing concentrated calcium and magnesium acetate. The rate of insulin addition to dialysate is controlled by adjusting input while monitoring the patient's blood glucose level.

What is claimed is:

1. A method for the continuous removal of protein-bound uremic toxins from the blood which enters the peritoneal cavity of a patient, comprising the steps of:

a) introducing from about 250 to about 1000 ml of dialysate into the peritoneal cavity, wherein protein-bound uremic toxins from the blood translocate into said dialysate;

b) removing the used dialysate from said peritoneal cavity;

c) separating the used dialysate through a filter into a protein-containing fraction and an ultrafiltrate fraction;

d) treating said ultrafiltrate fraction to remove waste products present in said ultrafiltrate fraction, thereby generating a purified ultrafiltrate fraction;

e) treating said protein-containing fraction from said filter to remove undesirable proteins and noxious uremic substances bound to proteins, thereby generating detoxified proteins;

f) combining said detoxified proteins and purified ultrafiltrate fraction to from regenerated dialysate;

g) reintroducing said regenerated dialysate into the peritoneal cavity.

2. The method of claim 1, further comprising the step of sterilizing said regenerated dialysate prior to reintroduction into the peritoneal cavity.

3. The method of claim 1, wherein said step c) comprises:

a") passing the used dialysate through a sieve, whereby cellular debris and mucoid material are removed therefrom; and b") passing said dialysate from which cellular debris and mucoid material have been removed through a filter, wherein said dialysate is separated into said protein-containing and ultrafiltrate fractions.

4. The method of claim 1, wherein said step e) comprises contacting said protein containing fraction with a matrix of materials which selectively removes noxious substances and undesirable proteins from said fraction.

5. The method of claim 1, wherein said step d) of treating said ultrafiltrate fraction comprises passing said ultrafiltrate fraction through sorbent phases comprising urease, zirconium phosphate, hydrated zirconium oxide and activated carbon.

6. The method of claim 1, wherein the overall flow rate through the cavity is about 2 to 3 liters per hour.

7. The method of claim 1 further comprising the step of adding to said regenerated dialysate one or more compounds selected from the group consisting of hormones, vitamins, sugars, minerals and other therapeutic agents.

* * * * *